(12) United States Patent
Matsumoto et al.

(10) Patent No.: US 7,402,710 B2
(45) Date of Patent: Jul. 22, 2008

(54) PROCESS FOR PRODUCING CHIRAL HYDROXYALDEHYDE COMPOUNDS

(75) Inventors: Kazuya Matsumoto, Boston, MA (US); Yasushi Kazuno, Sanbu-gun (JP); Norikazu Higashimura, Mobara (JP); Toshihisa Ohshima, Tokushima (JP); Haruhiko Sakuraba, Tokushima (JP)

(73) Assignee: Mitsui Chemicals, Inc., Tokyo (JP)

( * ) Notice: Subject to any disclaimer, the term of this patent is extended or adjusted under 35 U.S.C. 154(b) by 0 days.

(21) Appl. No.: 10/594,731

(22) PCT Filed: Mar. 28, 2005

(86) PCT No.: PCT/JP2005/005719

§ 371 (c)(1),
(2), (4) Date: Sep. 29, 2006

(87) PCT Pub. No.: WO2005/098012

PCT Pub. Date: Oct. 20, 2005

(65) Prior Publication Data

US 2007/0196906 A1    Aug. 23, 2007

(30) Foreign Application Priority Data

Mar. 29, 2004  (JP) .............................. 2004-095263

(51) Int. Cl.
*C07C 45/72* (2006.01)
(52) U.S. Cl. ...................................... 568/461
(58) Field of Classification Search ................. 568/461
See application file for complete search history.

(56) References Cited

U.S. PATENT DOCUMENTS 5,795,749 A    8/1998 Wong et al.

FOREIGN PATENT DOCUMENTS

| JP | 2003-230553 A | 8/2003 |
| WO | WO 03/006656 A2 | 1/2003 |
| WO | WO 03/006656 A3 | 1/2003 |
| WO | WO 03/077868 A2 | 9/2003 |
| WO | WO 03/077868 A3 | 9/2003 |

OTHER PUBLICATIONS

Carlos F. Barbas III, et al., "Deoxyribose-5-Phosphate Aldolase as a Synthetic Catalyst", Journal of the American Chemical Society, Feb. 28, 1990, pp. 2013-2014, vol. 112, No. 5, American Chemical Society.

Harrie J.M. Gijsen et al., "Unprecedented Asymmetric Aldol Reactions with Three Aldehyde Substrates Catalyzed by 2-Deoxyribose-5-phosphate Aldolase", Journal of the American Chemical Society, Sep. 7, 1994, pp. 8422-8423, vol. 116, No. 18, American Chemical Society.

Lihren Chen et al., "Deoxyribose-5-phosphate Aldolase as a Catalyst in Asymmetric Aldol Condensation", Journal of the American Chemical Society, Jan. 15, 1992, pp. 741-748, vol. 114, No. 2, American Chemical Society.

William A. Greenberg et al., "Development of an Efficient, Scalable, Aldolase-Catalyzed Process for Enantioselective Synthesis of Statin Intermediates", Apr. 20, 2004, pp. 5788-5793, vol. 101, No. 16, Proceedings of the National Academy of Sciences of the United States of America (PNAS).

Chi-Huey Wong et al., "Recombinant 2-Deoxyribose-5-phosphate Aldolase in Organic Synthesis: Use of Sequential Two-Substrate and Three-Substrate Aldol Reactions", Mar. 29, 1995, pp. 3333-3339, vol. 117, No. 12, American Chemical Society.

Timothy D. Machajewski et al., "The Catalytic Asymmetric Aldol Reaction", Angewandte Chemie International Edition, Apr. 17, 2000, pp. 1352-1374, vol. 39, No. 8, Wiley-VCH Verlag GmbH.

Haruhiko Sakuraba et al., "The First Crystal Structure of Archaeal Aldolase", The Journal of Biological Chemistry, pp. 10799-10806, vol. 278, No. 12, The American Society for Biochemistry and Molecular Biology.

Andreas Heine et al., "Analysis of the Class I Aldolase Binding Site Architecture Based on the Crystal Structure of 2-Deoxyribose-5-phosphate Aldolase at 0.99 Å Resolution", Journal of Molecular Biology (JMB), Oct. 29, 2004, vol. 343, No. 4, Elsevier Ltd.

K.E. Nelson et al., "Evidence for Lateral Gene Transfer Between Archaea and Bacteria from Genome Sequence of Thermotoga Maritima", Deoxyribose-Phosphate Aldolase (Phosphodeoxy Riboaldolase) (Deoxyriboaldolase), [online] Feb. 15, 2000, NCBI Entrez Protein, Accession Q9X1P5.

S.T. Fitz-Gibbon et al., "Genome Sequence of the Hyperthermophilic Crenarchaeon Pyrobaculum Aerophilum", Probable Deoxyribose-Phosphate Aldolase (Phosphodeoxyriboaldolase) (Deoxyriboaldolase), [online] Jun. 15, 2002, NCBI Entrez Protein, Accession Q8ZXK7.

*Primary Examiner*—Sikarl A Witherspoon
(74) *Attorney, Agent, or Firm*—Buchanan Ingersoll & Rooney PC

(57) ABSTRACT

An industrial process for producing hydroxyaldehydes efficiently, by solving the problems of conventional DERA, such as low stability against aldehydes, low catalytic activity for aldol condensation, and the difficulty of controlling the number of acetaldehyde molecules to be condensed, is provided.

According to the process, aldol condensation of a substituted or unsubstituted aliphatic aldehyde compound having 2 to 6 carbon atoms with acetaldehyde is conducted by using D-2-deoxyribose-5-phosphate aldolase which is highly stable against aldehydes and has high catalytic activity for aldol condensation, whereby a hydroxyaldehyde compound having the number of carbon atoms increased by two or four can be produced.

8 Claims, 1 Drawing Sheet

PROCESS FOR PRODUCING CHIRAL HYDROXYALDEHYDE COMPOUNDS

TECHNICAL FIELD

The present invention relates to a process for producing a hydroxyaldehyde compound, comprising conducting aldol condensation of a substituted or unsubstituted aliphatic aldehyde compound having 2 to 6 carbon atoms with a single molecule of acetaldehyde, or by further conducting aldol condensation with a second acetaldehyde molecule to produce the hydroxyaldehyde compound having the number of carbon atoms increased by two or four compared to that of the starting aliphatic aldehyde compound.

BACKGROUND ART

D-2-deoxyribose-5-phosphate aldolase (EC4.1.2.4) (hereinafter, referred to as "DERA" for short) is a generic name for an enzyme which catalyzes aldol condensation which synthesizes D-2-deoxyribose-5-phosphate from glyceraldehyde-3-phosphate and acetaldehyde as substrates, and a reverse reaction thereof (retro-aldol reaction). Reactivity of *Escherichia coli* (*E. coli*)-derived DERA was analyzed in detail, and reported to have a relatively wide spectrum of substrate-specificity, thus catalyze aldol condensation of various aldehydes to produce chiral hydroxyaldehydes (See Non-Patent Document 1).

Figure 1:
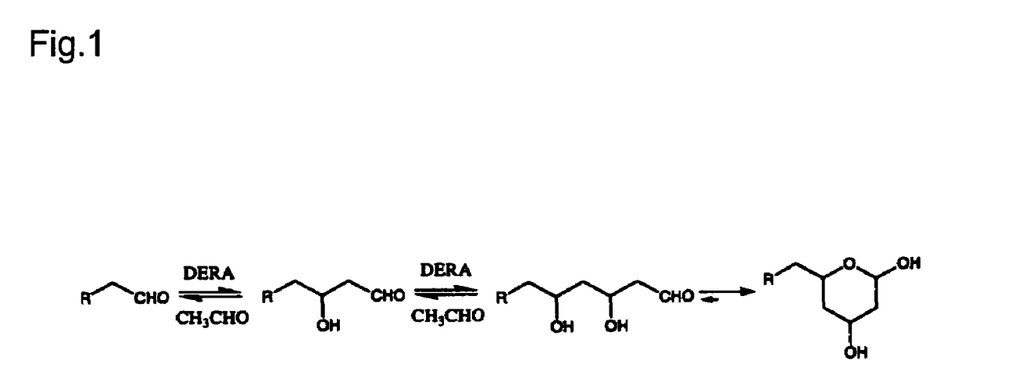
FIG. 1 is a schematic diagram illustrating sequential aldol reactions catalyzed by DERA.

As shown in the reaction scheme of FIG. 1, it is reported that in the aldol condensation of various aldehydes with acetaldehyde, a compound having the number of carbon atoms increased by four compared to that of the starting aldehyde is obtained by subjecting a hydroxyaldehyde, which is resulted from aldol condensation of a single molecule of aldehyde and a single molecule of acetaldehyde, to further aldol condensation with another single molecule of acetaldehyde. It has been reported that this compound resulting from aldol condensation with two molecules of acetaldehyde is produced as the main reaction product because the compound takes a stable lactol structure (See Non-Patent Document 2).

However, the conventionally known activity of DERA to various aldehydes as described above is reported to be extremely low, and to be less than 1/100 of the activity with respect to glyceraldehyde-3-phosphate and acetaldehyde, which are the original substrates (See Non-Patent Document 3). It is also reported that aldehydes are strong inhibitors to enzymes, and DERA is also inhibited by aldehydes (See Non-Patent Document 4). Accordingly, aldol condensation of these aldehydes requires a large amount of the enzyme. For example, Patent Document 1 described above discloses the synthesis of a 2,4,6-trideoxyhexose derivative via a 4-substituted-3-hydroxybutylaldehyde intermediate, wherein an increased amount of D-2-deoxyribose-5-phosphate aldolase to the degree of 125 U/mmol to 150 U/mmol was added, relative to the total number of moles of the substrates, namely, acetaldehyde and substituted acetaldehyde. Similarly, it is believed that even the reaction of condensation one acetaldehyde molecule requires the addition of an increased amount of the enzyme to the degree of 80 U/mmol to 100 U/mmol. Furthermore, for the purpose of alleviating inhibition, multiple addition of aldehydes and DERA is also being investigated (See Patent Document 2).

The aldol condensation reaction by DERA has another problem in controlling the number of acetaldehyde molecules to be condensed. Although the attempts of changing the concentration ratio of two aldehydes subjected to the aldol condensation or changing the amount of enzyme have been made, it has been difficult to control the number of acetaldehyde molecule, only except for the case of aldol condensation of several aldehydes having hydroxyl groups on the α-position or β-position, with acetaldehyde (See Non-Patent Document 5, Non-Patent Document 6 and Patent Document 3). Due to these problems, it has been difficult to practicalize the aldol condensation by DERA.

From the viewpoint of highly stable DERA, a thermally stable DERA which is derived from a hyperthermophilic bacterium, *Aeropyrum pernix*, has been reported (See Patent Document 4). This enzyme is reported to have high thermal stability and high stability against polar organic solvents such as methanol, ethanol and the like (See Non-Patent Document 8). Additionally, DERA derived from thermophilic bacteria such as *Thermotoga maritima, Thermus thermophilus* and the like have been reported, but nothing is reported concerning the stability against aldehydes, activity on aldol condensation or the like of these thermophilic bacterium-derived DERA (See Non-Patent Document 9).

In general, a thermophilic bacterium-derived enzyme exhibits high activity in a high temperature region near the original growth temperature, and has significantly low activity in the normal temperature region. In the case of the aldol condensation in which a highly reactive compound such as aldehyde is used as the substrate, a reaction in a high temperature region is predicted to be accompanied by various side reactions. Thus, it is necessary to perform the aldol reaction under low temperature conditions, and therefore, it is generally inconceivable to use a thermophilic bacterium-derived DERA for the reaction. Furthermore, it was difficult to deduce that the enzyme would have high stability against aldehydes, merely from the fact that the enzyme has high thermal stability, since aldehydes have a property of being reactive to the lysine residue or the like that are present in proteins.

[Patent Document 1] U.S. Pat. No. 5,795,749
[Patent Document 2] WO 03/006656
[Patent Document 3] WO 03/077868
[Patent Document 4] JP-A No. 2003-250553
[Non-Patent Document 1] J. Am. Chem. Soc., Vol. 112, pp. 2013-2014 (1990)
[Non-Patent Document 2] J. Am. Chem. Soc., Vol. 116, pp. 8422-8423 (1994)
[Non-Patent Document 3] J. Am. Chem. Soc., Vol. 114, pp. 741-748 (1992)
[Non-Patent Document 4] PNAS, Vol. 101, pp. 5788-5793 (2004)
[Non-Patent Document 5] J. Am. Chem. Soc., Vol. 117, pp. 3333-3339 (1995)
[Non-Patent Document 6] Angeu. Chem. Int. Ed., Vol. 39, pp. 1352-1374 (2000)
[Non-Patent Document 7] J. Am. Chem. Soc., Vol. 114, pp. 741-748 (1992)
[Non-Patent Document 8] J. Biol. Chem., Vol. 278, pp. 10799-10806 (2003)
[Non-Patent Document 9] J. Mol. Biol., Vol. 343, pp. 1019-1034 (2004)

DISCLOSURE OF THE INVENTION

It is an object of the present invention to provide an industrial process for producing hydroxyaldehydes efficiently, by solving the problems of conventional DERA, such as low stability against aldehydes, low catalytic activity for aldol condensation, and the difficulty of controlling the number of acetaldehyde molecules to be condensed.

The inventors have assiduously searched for a DERA having high stability against aldehydes and having high catalytic activity for aldol condensation. As a result, they found that DERA derived from hyperthermophilic bacteria, *Thermotoga maritima* and *Pyrobaculum aerophilum*, have remarkably high stability against aldehydes. Furthermore, they also found that although their activities at 25° C. on natural substrates, namely, glyceraldehyde-3-phosphate and acetaldehyde, are significantly low compared with the conventional *E. coli*-derived enzyme, their activities for aldol condensation reaction on non-natural substrates, such as aldehydes and acetaldehyde, are much higher than the activity of *E. coli*-derived DERA that has been reported previously. Moreover, they found that for DERA derived from the hyperthermophilic bacterium, *Pyrobaculum aerophilum*, it is not likely that the β-hydroxyaldehyde resulting from aldol condensation of a single molecule of aldehyde with a single molecule of acetaldehyde undergoes further aldol condensation reaction with another single molecule of acetaldehyde, and a β-hydroxyaldehyde having the number of carbon atoms increased by two is preferentially obtained. Thus, the invention has been completed.

For *Thermotoga maritima* and *Pyrobaculum aerophilum*, their genome information has been already disclosed (Nature, Vol. 399, pp. 323-329 (1999); Pro. Natl. Acad. Sci. U.S.A., Vol. 99, pp. 984-989 (2002)), and based on this information, it has been presumed that there exists a DNA sequence which is believed to encode DERAs of both strains, from the viewpoint of its homology with *E. coli*-derived DERA. However, no detailed analysis is conducted on these hyperthermophilic bacteria-derived DERAs, and it was also impossible to assume, prior to the present invention, that these DERAs have such effect. Thus, the invention is to demonstrate and disclose, for the first time, the effect of hyperthermophilic bacteria-derived DERAs on their applicability to various aldol condensation reactions which has been unknown.

Thus, the invention relates to:

[1] A process for producing a hydroxyaldehyde compound, comprising conducting aldol condensation of a substituted or unsubstituted aliphatic aldehyde compound having 2 to 6 carbon atoms with a single molecule of acetaldehyde to produce a hydroxyaldehyde compound having the number of carbon atoms increased by two, using D-2-deoxyribose-5-phosphate aldolase having a property of retaining 50% or greater of activity after treating at 25° C. for 30 minutes in an aqueous medium containing 100 mM of chloroacetaldehyde and

[2] A process for producing a hydroxyaldehyde compound, comprising conducting aldol condensation of a substituted or unsubstituted aliphatic aldehyde compound having 2 to 6 carbon atoms with two molecules of acetaldehyde to produce a hydroxyaldehyde compound having the number of carbon atoms increased by four, using D-2-deoxyribose-5-phosphate aldolase (or cells containing the enzyme or a lysate thereof) having a property of retaining 50% or greater of activity after treating at 25 C for 30 minutes in an aqueous medium containing 100 mM of chloroacetaldehyde.

According to the present invention, the productivity per reactor can be enhanced by using a small amount of DERA having high stability against aldehydes and high catalytic activity for aldol condensation. Further, it is possible to obtain a desired hydroxyaldehyde compound with high yield, by properly using a DERA which has high activity for aldol condensation of a single molecule of acetaldehyde, and a DERA which has high activity for aldol condensation of two molecules of acetaldehyde.

BEST MODE FOR CARRYING OUT THE INVENTION

The residual activity of DERA after the treatment at 25° C. for 30 minutes in an aqueous medium containing 100 mM chloroacetaldehyde is defined as the ratio of the total amount of 4-chloro-3-hydroxybutylaldehyde and 6-chloro-2,4,6-trideoxyhexose which are produced in a reaction started by the addition of 100 mM acetaldehyde at the final concentration and performed at 25° C. for 2 hrs following the treatment of DERA at 25° C. for 30 minutes in an aqueous solution containing 100 mM chloroacetaldehyde and 100 mM of buffer component at the appropriate pH value for the DERA being used in the present invention to the total amount of 4-chloro-3-hydroxybutylaldehyde and 6-chloro-2,4,6-trideoxyhexose in the control reaction which lacks the step of heat treatment of DERA. Moreover, in the present specification, the evaluation of the residual activity after a treatment at 25° C. for 30 minutes in an aqueous medium containing 100 mM of chloroacetaldehyde, is simply referred to as "evaluation of chloroacetaldehyde resistance", and the value of the residual activity after a treatment at 25° C. for 30 minutes in an aqueous medium containing 100 mM of chloroacetaldehyde may be abbreviated to "chloroacetaldehyde resistance value".

For the activity of DERA used in the present invention, the amount of enzyme which decomposes 1 μmol of D-2-deoxyribose-5-phosphate to D-glyceraldehyde-3-phosphate and acetaldehyde in 1 minute at 25° C. is defined as 1 U. The D-glyceraldehyde-3-phosphate produced by decomposition of D-2-deoxyribose-5-phosphate is quantified by the amount of decrease in NADH (reduced nicotinamide adenine dinucleotide), which results from conversion of D-glyceraldehyde-3-phosphate to dihydroxyacetone phosphate by triose phosphate isomerase and the subsequent reaction of dihydroxyacetone phosphate with glycerol-3-phosphate dehydrogenase.

The DERA used for the present invention is not limited, provided that it has a residual activity of 50% or greater after a treatment at 25° C. for 30 minutes in an aqueous medium containing 100 mM of chloroacetaldehyde. Suitable example of such DERAs includes a DERA having an amino acid sequence of SEQ ID NO: 2 or a DERA having an amino acid sequence of SEQ ID NO:4.

The DERA having an amino acid sequence of SEQ ID NO: 2 is obtained from, for example, *Thermotoga maritima* (JCM No. 10099) which is available from Japan Collection of Microorganisms (JCM). The amino acid sequence of SEQ ID NO: 2 may be a sequence having mutation introduced to the amino acid sequence of SEQ ID NO: 2 such that one to several amino acids are deleted or substituted by other amino acid residues, or other amino acid residues are inserted, as far as effects shown in the present invention are maintained.

The DERA having an amino acid sequence of SEQ ID NO: 4 is obtained from, for example, *Pyrobaculum aerophilum* (JCM No. 9630) which is available from JCM. The amino acid sequence of SEQ ID NO: 4 may be a sequence having mutation introduced to the amino acid sequence of SEQ ID NO: 4 such that one to several amino acids are deleted or substituted by other amino acid residues, or other amino acid residues are inserted, as far as effects shown in the present invention are maintained.

Recent progress in molecular biology and genetic engineering has made it possible, and also easier, to construct a genetically modified bacterium from arbitrary host by transforming the plasmid to which the above-mentioned gene of DERA and a regulatory region necessary for expression thereof was inserted. Considering such level of technology, a gene recombinant bacterium having the gene of DERA transfected into an arbitrary host is also included in the microorganism expressing DERA of the present invention. The regulatory region necessary for the gene expression as described herein refers to a promoter sequence (including an operator sequence regulating transcription), a ribosome-binding sequence (an SD sequence), a transcription termination sequence or the like. Examples of the promoter sequence include trp promoter of tryptophan operon derived from *E. coli*, lac promoter of lactose operon, PL promoter or PR promoter derived from lambda-phage, a gluconate synthase promoter (gnt) derived from *Bacillus subtilis*, an alkaline protease promoter (apr), a neutral protease promoter (npr), an α-amylase promoter (amy), and the like. Sequences specifically designed and modified, such as tac promoter, may also be used. Examples of the ribosome-binding sequence include such sequences derived from *E. coli* or *B. subtilis*, but are not particularly limited, provided that such a sequence functions in a desired host such as *E. coli* or *B. subtilis*. For example, a consensus sequence in which a sequence of 4 or more consecutive bases is complementary to the 3'-terminal region of 16S ribosomal RNA, may be prepared in DNA synthesis and used for the purpose. The transcription termination sequence is not essentially needed, but the ones independent of the ρ factor, such as a lipoprotein terminator, a trp operon terminator and the like can be used. These regulatory regions on the recombinant plasmid are preferably arranged in the order of the promoter sequence, the ribosome-binding sequence, the gene encoding DERA, and the transcription termination sequence, from the 5'-terminus. Specific examples of the plasmid described herein that can be used as vector include pBR322, pUC18, Bluescript II SK (+), pKK223-3, pSC101, pET15b (available from Novagen, Inc.) and the like, which have a region capable of self-replication in *E. coli*, and pUB110, pTZ4, pC194, ρ11, φ1, φ105 and the like, which have a region capable of autonomic replication in *B. subtilis*. In addition, examples of the plasmid that is capable of autonomic replication in two or more species of host and can be used as vector include pHV14, TRp7, YEp7 and pBS7. The arbitrary host as described herein is exemplified by *Escherichia coli* such as *E. coli* BL21 [DE3] strain (available from Novagen, Inc.) as a representative example, as described in the following Examples, but is not limited to *E. coli* in particular. Examples of the arbitrary host also include other microbial strains, such as bacteria belonging to Genus *Bacillus* such as *Bacillus subtilis*, yeasts and Actinomycetes.

The techniques of gene recombination such as transformation can be performed according to the methods described in *Molecular Cloning, A Laboratory Manual*, 2$^{nd}$ Edition, Coldspring Harbor Laboratory Press (1989), and the like. The transformed recombinant cells can be cultured under appropriate conditions, and DERA can be prepared from the culture product through known purification methods.

A hydroxyaldehyde compound having the number of carbon atoms increased by two compared to that of aliphatic aldehyde compound can be prepared by conducting an aldol condensation reaction of the substituted or unsubstituted aliphatic aldehyde compound having 2 to 6 carbon atoms with a single molecule of acetaldehyde, in an aqueous medium containing 100 mM of chloroacetaldehyde, in the presence of D-2-deoxyribose-5-phosphate aldolase having a property of retaining the residual activity of 50% or greater after a treatment at 25° C. for 30 minutes. This aldol condensation reaction is usually conducted in an aqueous solution. During the reaction, an appropriate buffering component may be added for the purpose of maintaining the optimal pH, or pH may be adjusted appropriately with acid or alkali. Furthermore, the reaction may be also conducted in the presence of an organic solvent which is miscible with water, or an organic solvent which is immiscible with water, to an extent of not inhibiting the reaction.

For the substituted or unsubstituted aliphatic aldehyde compound having 2 to 6 carbon atoms, the substituted aliphatic aldehyde compound having 2 to 6 carbon atoms is a compound in which a hydrogen atom bonded to an arbitrary position of the unsubstituted aliphatic aldehyde compound having 2 to 6 carbon atoms (except for the hydrogen atom of an aldehyde group) is substituted by a substituent. Such substitutent is not particularly limited as long as it does not adversely affect the aldol condensation reaction, and may be exemplified by a halogen atom, an azido group, a carboxyl group, an alkoxy group, an alkanoic acid group, and the like.

The substituted or unsubstituted aliphatic aldehyde compound having 2 to 6 carbon atoms may be exemplified by a compound represented by General Formula (1), General Formula (2), or General Formula (3). When these aliphatic aldehyde compounds are respectively subjected to aldol condensation with a single molecule of acetaldehyde, the compounds represented by General Formula (4), General Formula (5) and General Formula (6), which respectively correspond to the above aliphatic aldehyde compounds, are synthesized. Further, when the compound represented by General Formula (1) is subjected to aldol condensation with two molecules of acetaldehyde, a 3-5-hydroxyaldehyde compound represented by General Formula (7) is synthesized. Here, $R_1$ in General Formulae (1) to (7) is selected from a hydrogen atom, a hydroxyl group, a halogen atom, an azido group, a carboxyl group or an alkoxy group having 1 to 4 carbon atoms. $R_2$ is selected from a hydrogen atom, a hydroxyl group or a methyl group. $R_3$ is selected from a hydrogen atom or a hydroxyl group.

The compound represented by General Formula (2) may be exemplified by acetaldehyde, chloroacetaldehyde, glycolaldehyde, propionaldehyde, butylaldehyde, isobutylaldehyde, 3,4-dihydroxybutylaldehyde, malonate semialdehyde, succinate semialdehyde, adipate semialdehyde, or the like. Chloroacetaldehyde in particular significantly exhibits the effect of the invention, and thus is used suitably. When chloroacetaldehyde is subjected to aldol condensation with a single molecule of acetaldehyde, 4-chloro-3-hydroxybutylaldehyde having the number of carbon atoms increased by two compared to that of the chloroacetaldehyde is synthesized, and when the 4-chloro-3-hydroxybutylaldehyde is sequentially subjected to aldol condensation with a second acetaldehyde molecule, 6-chloro-2,4,6-trideoxyhexose having the number of carbon atoms increased by four compared to that of the chloroacetaldehyde is synthesized. The compound represented by General Formula (3) may be typically exemplified by D-glyceraldehyde, isobutylaldehyde, or the like. The compound represented by General Formula (4) may be exemplified by D-erythrose or 3,4-dihydroxybutylaldehyde.

The molar amount of acetaldehyde to be used with respect to the compound represented by General Formula (1), General Formula (2) or General Formula (3) is suitably set to be in the range of 0.5 molar equivalents to 3.0 molar equivalents. For example, when chloroacetaldehyde is subjected to aldol condensation with a single molecule of acetaldehyde to synthesize 4-chloro-3-hydroxybutylaldehyde, the molar amount of acetaldehyde to be used with respect to chloroacetaldehyde is typically set in a range of 0.5 molar equivalents to 1 molar equivalent. More preferably, when DERA having low activity of catalyzing aldol condensation with two molecules of acetaldehyde, such as *Pyrobaculum aerophilum* derived DERA is used, the molar amount of acetaldehyde to be used with respect to chloroacetaldehyde can be set to be in the range of 0.5 molar equivalents to 3 molar equivalents, so as to synthesize 4-chloro-3-hydroxybutylaldehyde with good yield.

Further, when chloroacetaldehyde is subjected to aldol condensation with two molecules of acetaldehyde to synthesize 6-chloro-2,4,6-trideoxyhexose, the molar amount of acetaldehyde to be used with respect to chloroacetaldehyde is typically set in a range of 2 molar equivalents to 3 molar equivalents. The use of DERA having high activity of catalyzing aldol condensation with two molecules of acetaldehyde, such as *Thermotoga maritima*-derived DERA, is more desirable for the synthesis of 6-chloro-2,4,6-trideoxyhexose with good yield.

The amount of DERA to be used in the aforementioned reaction is defined within the following ranges. When a single molecule of acetaldehyde is subjected to aldol condensation to synthesize 3-hydroxyaldehyde, DERA can be used to react at a ratio of 0.1 U/mmol to 80 U/mmol, relative to the total number of moles of the aldehyde compound represented by General Formula (1), General Formula (2) or General Formula (3), and acetaldehyde.

When two molecules of acetaldehyde are subjected to aldol condensation to synthesize 3,5-dihydroxyaldehyde, DERA can be used to react at a ratio of 0.1 U/mmol to 120 U/mmol, relative to the total number of moles of the aldehyde compound represented by General Formula (1) and acetaldehyde.

For the present reaction described above, the pH range and the reaction temperature may be suitably selected to provide optimal conditions by taking account of the yield of the desired product, and the like. For example, the pH range of the reaction solution is preferably pH 4 to 12, and more preferably pH 5 to 9. In preparing a buffer solution of a pH value in such range, any pH buffering agent having sufficient buffering effect can be used. The reaction temperature can be selected from a range of 0° C. to 100° C., but is preferably in the range of 0° C. to 40° C., and more preferably in the range of 0° C. to 25° C.

The time needed for the reaction may be favorably set to provide the highest yield of the desired product. The desired product can be separated and recovered from the reaction solution by known purification methods such as extraction, azeotropic distillation, crystallization and the like.

Hereinafter, the present invention will be described in more detail by way of Examples, but the invention is not intended to be limited by these Examples.

EXAMPLE 1

Preparation of DERA Derived from *Thermotoga maritima*

[1] Preparation of *Thermotoga maritima* Chromosomal DNA

JCM237 medium [prepared as follows: a composition comprising 5.0 g of soluble starch, 0.5 g of $KH_2PO_4$, 15.0 ml of mineral containing solution (containing 1.5 g of nitrilotriacetic acid, 3.0 g of $MgSO_4.7H_2O$, 0.5 g of $MnSO_4.xH_2O$, 1.0 g of NaCl, 0.1 g of $FeSO_4.7H_2O$, 0.1 g of $CoSO_4.7H_2O$, 0.1 g of $ZnSO_4.7H_2O$, 0.01 g of $CuSO_4.5H_2O$, 0.01 g of AlK$(SO_4)_2$, 0.01 g of $H_3BO_3$, and 0.01 g of $Na_2MoO_4.2H_2O$ per 1 L of distilled water; Preparation is done by dissolving nitrilotriacetic acid, followed by the adjustment of the pH value to 6.5 with KOH, the addition of the remaining minerals, and the adjustment of the final pH value to 7.0), 2.0 mg of $NiCl_2.H_2O$, 20.0 g of NaCl, 0.5 g of Bacto yeast extract (available from Difco Laboratories, Inc.), 1.0 mg of resazurin, 0.5 g of $Na_2S-9H_2O$, 250 ml of artificial seawater (a composition prepared by dissolving 27.7 g of NaCl, 7.0 g of $MgSO_4.7H_2O$, 5.5 g of $MgCl_2.6H_2O$, 0.65 g of KCl, 0.1 g of NaBr, 30.0 mg of $H_3BO_3$, 15.0 mg of $SrCl_2.6H_2O$, 10.0 mg of citric acid, 0.05 mg of KI, and 2.25 g of $CaCl_2.H_2O$ per 1 L of distilled water), and 750 ml of distilled water is prepared by mixing all the components except $Na_2S.9H_2O$, and adjusting pH to 6.5 with $H_2SO_4$. The composition is sterilized by filtration in a nitrogen atmosphere. The composition is used as a 5% solution to neutralize $Na_2S.9H_2O$, and is sterilized under high pressure (121° C., 20 minutes) in a nitrogen atmosphere. Before inoculation, sterilized $Na_2S.9H_2O$ is added, and pH is adjusted to 6.5, if necessary] was used for culturing *Thermotoga maritima*. The preserved strain (JCM No. 10099) was incubated under stirring with a magnetic stirrer at 80° C. for 24 to 96 hours, while maintaining an anaerobic condition by nitrogen purging after deaeration, to prepare 2 L of the culture solution. After completion of the incubation, the bacteria in the resulting culture solution were harvested by centrifugation (5000 g, 10 minutes), and were washed with 3% NaCl. In 8 ml of TE buffer solution (10 mM Tris-HCl (pH 7.5), 1 mM EDTA), 2 g of the bacteria as wet bacterial weight was suspended. This bacterial suspension was mixed with 2 ml of a 10 mg/ml lysozyme solution and 100 µl of a 10 mg/ml RNase solution, and the mixture was incubated at 37° C. for 30 minutes. Then, 50 µl of a 20 mg/ml Proteinase K solution was added to the mixture, and after 10 minutes, 1 ml of a 30 mg/ml sodium N-lauroylsarcosine solution was added to the mixture. The resulting mixture was further incubated for 45 minutes. An equivalent volume of CI (chloroform:isoamyl alcohol=24:1) was added to the resulting solution, with mild blending, and the mixture was centrifuged (7000 g, 15 minutes) to separate the aqueous layer. The same operation was repeated once more, and then a PCI treatment (water-equilibrated phenol:CI=1:1) was repeated twice in the same manner as in the CI treatment. The CI treatment was further carried out twice, then a 0.1-fold amount of 3 M sodium acetate was added to the aqueous layer with stirring, and an equivalent volume of isopropanol was added with gentle stirring. Precipitated DNA was wound up on a disposable tube, washed with 70% ethanol, dried, and dissolved in 500 µl of TE buffer solution, so as to obtain the *Thermotoga maritima* chromosomal DNA.

[2] Cloning of *Thermotoga maritima* DERA Gene, and Preparation of *E. coli* Strain Expressing DERA A DNA fragment containing *Thermotoga maritima*-derived DERA gene of SEQ ID NO: 1 was obtained by PCR using oligonucleotides having the sequences of SEQ ID NO: 5 and SEQ ID NO: 6 as primers, and by using *Thermotoga maritima* chromosomal DNA as template. The obtained DNA fragment was treated with restriction enzymes NdeI and BamHI, and was ligated to a commercial expression vector pET15b (available from Novagen, Inc.) which had been treated similarly with NdeI and BamHI, to obtain a plasmid expressing *Thermotoga maritima*-derived DERA, pET15b-TM1559. This expression plasmid was used to transform *E. coli* BL21 [DE3] strain (available from Novagen, Inc.), so as to obtain *E. coli* BL21 [DE3]/pET15b-TM1559 expressing *Thermotoga maritima*-derived DERA.

[3] Purification of *Thermotoga maritima*-Derived DERA from Recombinant *E. coli*

The recombinant *E. coli* strain BL21 [DE3]/pET15b-TM1559 was inoculated to 100 ml of SB medium (12 g of tryptone, 24 g of yeast extract, 5 ml of glycerol, 12.5 g of $K_2HPO_4$, and 3.8 g of $KH_2PO_4$ in 1 L) containing 50 µg/ml of ampicillin, and was cultured at 37° C. until $OD_{660}$ reached 0.6. Then, IPTG (isopropyl-β-thiogalactopyranoside) was added to a final concentration of 1 mM, and the culture was further continued for 3 hours. After completion of the culture, the bacteria were harvested by centrifugation (5000 g, 10 minutes), washed with a 0.85% NaCl solution, and were suspended in a 10 mM Tris-HCl buffer solution (pH 7.5) with an amount of 9 times of the wet bacterial weight. The bacterial cells were disrupted by sonication and then centrifuged, and the supernatant was used as the crude enzyme solution. The crude enzyme solution was heated at 80° C. for 10 minutes, and the denatured insoluble proteins were removed by centrifugation. A metal affinity column coordinated with nickel (HiTrap affinity column (available from Pharmacia Biotech, Inc.)) was equilibrated with a 10 mM Tris-HCl (pH 7.5) buffer solution containing 0.5 M NaCl and 10 mM imidazole, and then the crude enzyme solution from which the insoluble proteins resulting from the heat treatment were removed, was applied thereon, and the active fractions were collected by eluting the protein with solution containing 0.1 M, 0.2 M, 0.3 M, 0.4 M, and 0.5 M of imidazole. The purity of *Thermotoga maritima*-derived DERA thus obtained was analyzed by SDS-PAGE to confirm homogeneity. The amount of the protein was quantified by using a Bio-Rad Protein Assay kit (available from Bio-Rad Laboratories, Inc.).

EXAMPLE 2

Preparation of DERA Derived from *Pyrobaculum aerophilum*

JCM215 medium [prepared as follows: 125 ml of a marine culture medium/synthetic seawater mixture (a solution prepared by dissolving 47.15 g of NaCl, 18.10 g of $MgCl_2.6H_2O$, 7.0 g of $MgSO_4.7H_2O$, 3.13 g of $CaCl_2.2H_2O$, 3.24 g of $Na_2SO_4$, 0.1 g of $Na_2CO_3$, 0.1 g of NaBr, 80.0 mg of KBr, 72.0 mg of $SrCl_2.6H_2O$, 52.0 mg of $H_3BO_3$, 8.1 mg of $Na_2HPO_4$, 2.4 mg of NaF, 0.4 mg of sodium silicate, and 0.05 mg of KI in 1 L of distilled water), 10.0 ml of mineral containing solution (a mineral solution comprising 1.5 g of nitrilotriacetic acid, 3.0 g of $MgSO_4.7H_2O$, 0.5 g of $MnSO_4.xH_2O$, 1.0 g of NaCl, 0.1 g of $FeSO_4.7H_2O$, 0.1 g of $CoSO_4.7H_2O$, 0.1 g of $ZnSO_4.7H_2O$, 0.01 g of $CuSO_4.5H_2O$, 0.01 g of $AlK(SO_4)_2$, 0.01 g $H_3BO_3$, and 0.01 g of $Na_2MoO_4.2H_2O$ per 1 L of distilled water; Preparation is done by dissolving nitrilotriacetic acid, followed by the adjustment of the pH value to 6.5 with KOH, the addition of the remaining minerals, and the adjustment of the final pH value to 7.0), 2.0 mg of $Fe(NH_4)_2.6H_2O$, 0.25 g of $NH_4Cl$, 2.0 mg of $(NH_4)_2Ni(SO_4)_2.6H_2O$, 0.1 mg of $Na_2SeO_4$, 0.1 mg of $NaWO_4.2H_2O$, 2.2 g of $NaHCO_3$, 0.07 g of $KH_2PO_4$, 0.5 g of Bacto yeast extract (available from Difco Laboratories, Inc.), 1.0 g of $NaS_2O_3.5H_2O$, and 865.0 ml of distilled water were mixed and dissolved, and the pH value of the solution was adjusted to 7.0 with 1 N $H_2SO_4$, and then the resulting solution was sterilized by filtration. The medium was placed in an incubator under an atmosphere of gas containing nitrogen, carbon dioxide and oxygen at a mixing ratio of 80:20:1] was used for culturing *Pyrobaculum aerophilum*. After inoculation, the culture was performed at 95° C. with a pressure of 200 kPa. The *Pyrobaculum aerophilum* chromosomal DNA was prepared from the preserved strain (JCM No. 9630) in the same manner as in Example 1. A DNA fragment containing *Pyrobaculum aerophilum*-derived DERA gene of SEQ ID NO: 3 was obtained by PCR using oligonucleotides having the sequences of SEQ ID NO: 7 and SEQ ID NO: 8 as primers, and by using the *Pyrobaculum aerophilum* chromosomal DNA as template. The initiation codon GTG of the *Pyrobaculum aerophilum*-derived DERA gene was changed to ATG for the purpose of expression in *E. coli*. The sequence of SEQ ID NO: 3 indicates the DNA sequence after the change.

The obtained DNA fragment was treated with restriction enzymes NdeI and BamHI, and was ligated to a commercial expression vector pET15b which had been treated similarly with NdeI and BamHI, to obtain a plasmid expressing *Pyrobaculum aerophilum*-derived DERA, pET15b-PAE1231. This expression plasmid was used to transform *E. coli* BL21 [DE3] strain, so as to obtain *E. coli* strain BL21 [DE3]/pET15b-PAE1231 expressing *Pyrobaculum aerophilum*-derived DERA.

Purification of the *Pyrobaculum aerophilum*-derived DERA from the recombinant *E. coli* strain BL21 [DE3]/pET15b-PAE1231 was performed according to the same method described in [3] of Example 1.

Reference Example 1

Purification of *E. coli*-Derived DERA

A DNA fragment containing *E. coli*-derived DERA gene was obtained from cultured bacterial cells of *E. coli* W3110

(ATCC No. 27325) which is available from the American Type Culture Collection (ATCC), by PCR using oligonucleotides having the sequences of SEQ ID NO: 9 and SEQ ID NO: 10 as primers, and by using the *E. coli* chromosomal DNA prepared in the same manner as in Example 1, as template. This DNA fragment containing *E. coli*-derived DERA gene was treated with restriction enzymes NdeI and BamHI, and was ligated to a commercial expression vector pET11b (available from Novagen, Inc.) which had been treated similarly with NdeI and BamHI, to obtain a plasmid expressing *E. coli*-derived DERA, pET11b-DERA. This expression plasmid was used to transform *E. coli* BL21 [DE3] strain to obtain *E. coli* strain BL21 [DE3]/pET11b-DERA expressing *E. coli*-derived DERA. A crude enzyme solution was prepared from the recombinant *E. coli* according to the method described in Example 1, which was fractionated by the ammonium sulfate precipitation method (50 to 70% of the saturation concentration), and then was dialyzed against a 50 mM Tris-HCl (pH 7.5) buffer solution. This dialyzed crude enzyme solution was applied to Phenyl 5PW hydrophobic chromatography (manufactured by Tosoh Corp.) and the proteins were eluted with 50 mM Tris-HCl (pH 7.5) buffer with linear concentration gradient of ammonium sulfate from 1 to 0 M. The collected active fractions were analyzed by SDS-PAGE to confirm homogeneous purification of *E. coli*-derived DERA. The amount of proteins was quantified by using a Bio-Rad Protein Assay kit.

EXAMPLE 3

Comparison of Activity for D-2-deoxyribose-5-phosphate Decomposition

The activities of *Thermotoga maritima*-derived DERA obtained in Example 1, *Pyrobaculum aerophilum*-derived DERA obtained in Example 2, and *E. coli*-derived DERA obtained in Reference Example 1, for D-2-deoxyribose-5-phosphate decomposition at 25° C. were measured. The measurement was performed by converting D-glyceraldehyde-3-phosphate, which was resulted from the decomposition of D-2-deoxyribose-5-phosphate by DERA, to dihydroxyacetone phosphate with triose phosphate isomerase, and the subsequent reaction of dihydroxyacetone phosphate with glycerol-3-phosphate dehydrogenase. The quantification was performed by measuring the consumed NADH by glycerol-3-phosphate dehydrogenase.

The components excluding D-2-deoxyribose-5-phosphate, triose phosphate isomerase, glycerol-3-phosphate dehydrogenase, and NADH from 1 ml of the activity measurement solution (50 mM of triethanolamine-HCl (pH 7.5), 0.5 mM of D-2-deoxyribose-5-phosphate, 3.9 U of triose phosphate isomerase (available from Sigma-Aldrich Co.), 11 U of glycerol-3-phosphate dehydrogenase (available from Sigma-Aldrich Co.), 0.12 mM of NADH, and the active fraction subject to measurement), were incubated at a constant temperature of 25° C. for 3 minutes, and then the remaining components were added thereto to start the measurement. While keeping the temperature at 25° C., the decrease in the absorbance at 340 nm was measured for 1 minute using an appropriate spectrophotometer. One unit (U) of DERA activity was defined as the amount of enzyme required to reduce 1 μmol of NADH per 1 minute at 25° C. The molar absorption coefficient of NADH at 340 nm was taken as 6.22 mM$^{-1}$ cm$^{-1}$. The enzyme activities (U) thus measured of *Thermotoga maritima*-derived DERA, *Pyrobaculum aerophilum*-derived DERA and *E. coli*-derived DERA at 25° C. per 1 mg of DERA are presented in Table 1.

TABLE 1

| Enzyme | Enzyme Activity |
|---|---|
| *Thermotoga maritima*-derived DERA | 0.58 U |
| *Pyrobaculum aerophilum*-derived DERA | 0.10 U |
| *E. coli*-derived DERA | 61.1 U |

EXAMPLE 4

Evaluation of Resistance to Chloroacetaldehyde

In a 100 mM citric acid-sodium citrate buffer solution (pH 6.5) containing 100 mM of chloroacetaldehyde, 250 μg of *Thermotoga maritima*-derived DERA was added, and the mixture was incubated at 25° C. for 30 minutes. After the incubation, acetaldehyde was added to the solution at a concentration of 100 mM, and an aldol condensation reaction was performed at 25° C. for 2 hours. For the control, 250 μg of *Thermotoga maritima*-derived DERA was added to a 100 mM citric acid-sodium citrate buffer solution (pH 6.5) containing 100 mM of chloroacetaldehyde, followed by the addition of acetaldehyde to the solution at a concentration of 100 mM, and then aldol condensation reaction was performed at 25° C. for 2 hours. The reaction was terminated by filtering the reaction solution through an ULTRAFREE-MC filter (manufactured by Millipore Corp.) to remove the proteins, and the amounts of 4-chloro-3-hydroxybutylaldehyde and 6-chloro-2,4,6-trideoxyhexose produced were quantified by HPLC analysis. The ratio of the total amount of the produced 4-chloro-3-hydroxybutylaldehyde and 6-chloro-2,4,6-trideoxyhexose to the corresponding amount in the control was calculated.

Likewise, to a 100 mM acetic acid-sodium acetate buffer solution (pH 5.5) containing 100 mM of chloroacetaldehyde, 250 μg of *Pyrobaculum aerophilum*-derived DERA was added, and the solution was incubated at 25° C. for 30 minutes. After the incubation, acetaldehyde was added to the solution at a concentration of 100 mM, and aldol condensation reaction was performed at 25° C. for 2 hours. For the control, 250 μg of *Pyrobaculum aerophilum*-derived DERA was added to a 100 mM acetic acid-sodium acetate buffer solution (pH 5.5) containing 100 mM of chloroacetaldehyde, followed by the addition of acetaldehyde at a concentration of 100 mM, and aldol condensation reaction was performed at 25° C. for 2 hours. The reaction was terminated by filtering the reaction solution through an ULTRAFREE-MC filter (manufactured by Millipore Corp.) to remove the proteins, and the amounts of 4-chloro-3-hydroxybutylaldehyde and 6-chloro-2,4,6-trideoxyhexose produced were quantified by HPLC analysis. The ratio of the total amount of the produced 4-chloro-3-hydroxybutylaldehyde and 6-chloro-2,4,6-trideoxyhexose to the corresponding amount in the control was calculated.

Likewise, 250 μg of *E. coli*-derived DERA was added to a 100 mM Tris-HCl buffer solution (pH 7.5) containing 100 mM of chloroacetaldehyde, and the solution was incubated at 25° C. for 30 minutes. After the incubation, acetaldehyde was added to the solution at a concentration of 100 mM, and aldol condensation reaction was performed at 25° C. for 2 hours. For the control, 250 μg of *Pyrobaculum aerophilum*-derived DERA was added to a 100 mM Tris-HCl buffer solution (pH 7.5) containing 100 mM of chloroacetaldehyde, followed by the addition of acetaldehyde to the solution at a concentration of 100 mM, and an aldol condensation reaction was performed at 25° C. for 2 hours. The reaction was terminated by filtering the reaction solution through an ULTRAFREE-MC filter (manufactured by Millipore Corp.) to remove the proteins, and the produced amounts of 4-chloro-3-hydroxybutylaldehyde and 6-chloro-2,4,6-trideoxyhexose were quantified by HPLC analysis. The ratio of the total amount of the produced 4-chloro-3-hydroxybutylaldehyde and 6-chloro-2,4,6-trideoxyhexose to the corresponding amount in the control was calculated.

The results of evaluation for the resistance to chloroacetaldehyde of *Thermotoga maritima*-derived DERA, *Pyrobaculum aerophilum*-derived DERA and *E. coli*-derived DERA by measuring the amount of 4-chloro-3-hydroxybutylaldehyde are presented in Table 2.

Method for Quantification of 4-chloro-3-hydroxybutylaldehyde and 6-chloro-2,4,6-trideoxyhexose by High Performance Liquid Chromatography (HPLC)

Analysis was performed by using a Develosil RPAQEOUS column (manufactured by Nomura Chemical Co., Ltd.) as an HPLC column, at a column temperature of 40° C. with water as the eluent. The applied amount was 20 µl, and the detection was performed by using a RI detector (manufactured by JASCO Corp.).

TABLE 2

| Enzyme | Chloroacetaldehyde resistance value (%) |
| --- | --- |
| *Thermotoga maritima*-derived DERA | 133 |
| *Pyrobaculum aerophilum*-derived DERA | 98 |
| *E. coli*-derived DERA | 15 |

EXAMPLE 5

Aldol Condensation of Chloroacetaldehyde and Acetaldehyde by *Thermotoga maritima*-Derived DERA Aldol condensation reaction was performed at 25° C. for 24 hours after the addition of 400 µg (0.23 U) of *Thermotoga maritima*-derived DERA to 1 ml of a reaction solution comprising 100 mM citric acid-sodium citrate buffer solution (pH 6.5), 300 mM acetaldehyde, and 100 mM chloroacetaldehyde. The reaction solution was filtered through an ULTRAFREE-MC filter (manufactured by Millipore Corp.) to remove the proteins, and then the total amount of the produced 4-chloro-3-hydroxybutylaldehyde and 6-chloro-2,4,6-trideoxyhexose was quantified by HPLC. The conversion rate of chloroacetaldehyde determined from the total amount of the products was 95%. The conversion rate of chloroacetaldehyde determined from the amount of 6-chloro-2,4,6-trideoxyhexose produced was 90%. The reaction solution was extracted with twice the volume of ethyl acetate three times, and the three fractions of ethyl acetate phase were combined and concentrated under reduced pressure. The concentrate was dissolved in a small amount of ethyl acetate, and the solution was applied to silica gel column chromatography. The solution was eluted with ethyl acetate/hexane(9:1) to fractionate 4-chloro-3-hydroxybutylaldehyde and 6-chloro-2,4,6-trideoxyhexose. The products separated by the column were respectively analyzed by $^1$H-NMR and $^{13}$C-NMR, and it was confirmed that the products coincided with the reports in Patent Document 1 and Non-Patent Document 2.

EXAMPLE 6

Aldol Condensation of Chloroacetaldehyde and Acetaldehyde by *Pyrobaculum aerophilum*-Derived DERA Aldol condensation reaction was performed at 25° C. for 24 hours after the addition of 400 µg (0.04 U) of *Pyrobaculum aerophilum*-derived DERA to 1 ml of a reaction solution comprising 100 mM acetic acid-sodium acetate buffer solution (pH 5.5), 300 mM acetaldehyde, and 100 mM chloroacetaldehyde. The reaction solution was filtered through an ULTRAFREE-MC filter (manufactured by Millipore Corp.) to remove the proteins, and then the total amount of 4-chloro-3-hydroxybutylaldehyde and 6-chloro-2,4,6-trideoxyhexose produced was quantified by HPLC. The conversion rate of chloroacetaldehyde determined from the total amount the products was 93%. The conversion rate of chloroacetaldehyde determined from the amount of 6-chloro-2,4,6-trideoxyhexose produced was 50%. The reaction solution was extracted with twice the volume of ethyl acetate three times, and the three fractions of ethyl acetate phase were combined and concentrated under reduced pressure. The concentrate was dissolved in a small amount of ethyl acetate, and the solution was applied to silica gel column chromatography. The solution was eluted with ethyl acetate/hexane (9:1), to fractionate 4-chloro-3-hydroxybutylaldehyde and 6-chloro-2,4,6-trideoxyhexose. The column separation products were respectively analyzed by $^1$H-NMR and $^{13}$C-NMR, and it was confirmed that the products coincided with the reports in Patent Document 1 and Non-Patent Document 2.

Reference Example 2

Aldol Condensation of Chloroacetaldehyde and Acetaldehyde by *E. coli*-Derived DERA Aldol condensation reaction was performed at 25° C. for 24 hours after the addition of 400 µg (24.4 U) of *E. coli*-derived DERA to 1 ml of a reaction solution comprising 100 mM Tris-HCl buffer solution (pH 7.5), 300 mM acetaldehyde (available from Junsei Chemical Co., Ltd.), and 100 mM chloroacetaldehyde (available from Tokyo Chemical Industry Co., Ltd.). The reaction solution was filtered through an ULTRAFREE-MC filter (manufactured by Millipore Corp.) to remove the proteins, and then the total amount of 4-chloro-3-hydroxybutylaldehyde and 6-chloro-2,4,6-trideoxyhexose produced was quantified by HPLC. The conversion rate of chloroacetaldehyde determined from the total amount of the products was 4%.

EXAMPLE 7

Process for Synthesizing 4-chloro-3-hydroxybutylaldehyde by Subjecting Chloroacetaldehyde to Aldol Condensation with a Single Molecule of Acetaldehyde Aldol condensation reaction was performed at 25° C. for 24 hours after the addition of 400 µg (0.04 U) of *Pyrobaculum aerophilum*-derived DERA to 1 ml of a reaction solution comprising 100 mM acetic acid-sodium acetate buffer solution (pH 5.5), 100 mM acetaldehyde, and 100 mM chloroacetaldehyde. The reaction solution was filtered through an ULTRAFREE-MC filter (manufactured by Millipore Corp.) to remove the proteins, and the total amount of 4-chloro-3-hydroxybutylaldehyde and 6-chloro-2,4,6-trideoxyhexose produced was quantified by HPLC. The conversion rate of chloroacetaldehyde determined from the total amount of the products was 90%. The conversion rate of chloroacetaldehyde determined from the amount of 4-chloro-3-hydroxybutylaldehyde produced was 80%. The reaction solution was extracted with twice the volume of ethyl acetate three times, the ethyl acetate layers were combined, and ethyl acetate was evaporated under reduced pressure. The obtained oily product was dissolved in a small amount of ethyl acetate, and subjected to silica gel chromatography with ethyl acetate/n-hexane (9:1) as the eluent to isolate 4-chloro-3-hydroxybutylaldehyde. The isolated 4-chloro-3-hydroxybutylaldehyde was analyzed by $^1$H-NMR and $^{13}$C-NMR, and it was confirmed that the product coincided with the report in Non-Patent Document 2, and was confirmed to be 4-chloro-3-hydroxybutylaldehyde. Furthermore, the optical purity measured by HPLC analysis was verified to be 97.8% ee.

Analysis of Optical Purity by HPLC

The reaction solution was cooled to 4° C. and was adjusted to pH 9.0 with 10% sodium hydroxide aqueous solution. Then, sodium borohydride was added, and the mixture was stirred for 30 minutes. The reaction solution was adjusted to pH 6.0 with 2 N hydrochloric acid in order to decompose the remaining sodium borohydride. Then, the reaction solution was extracted with twice the volume of ethyl acetate three times, the ethyl acetate layers were combined, and ethyl acetate was evaporated under reduced pressure. The obtained oily product was dissolved in a small amount of n-hexane/ethanol (50:50), and analyzed by HPLC. Analysis was performed by using a CHIRALPAK AD-H column (manufactured by Daicel Chemical Industries, Ltd.) as the HPLC column, at a column temperature of 40° C., with n-hexane/ethanol (92.5:7.5) as the eluent. The amount applied was 10 μl, and the detection was performed by using a RI detector (manufactured by JASCO Corp.).

EXAMPLE 8

Aldol Condensation of Various Aliphatic Aldehydes and Acetaldehyde by *Thermotoga maritima*-Derived DERA Aldol condensation reaction was performed at 25° C. after the addition of 400 μg (0.23 U) of *Thermotoga maritima*-derived DERA to 1 ml of a reaction solution comprising 100 mM citric acid-sodium citrate buffer solution (pH 6.5), 100 mM acetaldehyde, and 100 mM each of various aliphatic aldehydes (propionaldehyde, butylaldehyde, n-valeraldehyde, isobutylaldehyde, adipate semialdehyde methyl ester, and succinate semialdehyde).

The reaction solution was filtered through an ULTRAFREE-MC filter (manufactured by Millipore Corp.) to remove the proteins, and then the compounds produced by aldol condensation reaction of various aliphatic aldehydes and acetaldehyde were detected by means of the spots formed by thin layer chromatography (TLC) analysis. For all of the aliphatic aldehydes used as substrates in the reaction, the corresponding products of aldol condensation with acetaldehyde were detected.

TLC Analysis Conditions

Silica gel plate: Silica Gel 60 (manufactured by Merck & Co., Inc.)

Developing solution: Ethyl acetate: n-hexane=9:1

Spotted amount: 1 μl of reaction solution

Detecting method: 12-molybdo(VI)phosphoric acid n-hydrate (available from Wako Pure Chemical Industries, Ltd.) was dissolved in ethanol to make 7% solution, and a silica gel plate having samples applied thereon was immersed in the solution and heated for color development.

EXAMPLE 9

Aldol Condensation of Various Aliphatic Aldehydes with Acetaldehyde by *Pyrobaculum aerophilum*-Derived DERA Aldol condensation reaction was performed at 25° C. after the addition of 400 μg (0.04 U) of *Pyrobaculum aerophilum*-derived DERA to 1 ml of a reaction solution comprising 100 mM acetic acid-sodium acetate buffer solution (pH 5.5), 100 mM acetaldehyde, and 100 mM each of various aliphatic aldehydes (propionaldehyde, butylaldehyde, n-valeraldehyde, isobutylaldehyde, adipate semialdehyde methyl ester, and succinate semialdehyde).

The reaction solution was filtered through an ULTRAFREE-MC filter (manufactured by Millipore Corp.) to remove the proteins, and then the aldol condensation reaction compounds formed from various aliphatic aldehydes and acetaldehyde were detected by means of the spots formed by thin layer chromatography (TLC) analysis.

For all of the aliphatic aldehydes used as substrates in the reaction, the corresponding products of aldol condensation with acetaldehyde were detected.

TLC Analysis Conditions

Silica gel plate: Silica Gel 60 (manufactured by Merck & Co., Inc.)

Developing solution: Ethyl acetate: n-hexane=9:1

Spotted amount: 1 μl of reaction solution

Detecting method: 12-molybdo(VI)phosphoric acid n-hydrate (available from Wako Pure Chemical Industries, Ltd.) was dissolved in ethanol to make 71 solution, and a silica gel plate having samples applied thereon was immersed in the solution and heated for color development.

INDUSTRIAL APPLICABILITY

DERA derived from hyperthermophilic bacteria and the like, which is used in the producing process of the present invention, has high catalytic activity for the aldol condensation reaction using non-natural substrates, and has high enzyme stability even at high substrate concentrations. Thus, the producing process of the invention can enhance the productivity of chiral hydroxyaldehyde compounds per reactor, compared with conventional processes using *E. coli*-derived DERA.

---

The invention claimed is:

1. A process for producing a hydroxyaldehyde compound, comprising conducting aldol condensation of a substituted or unsubstituted aliphatic aldehyde compound having 2 to 6 carbon atoms with a single molecule of acetaldehyde to produce a hydroxyaldehyde compound having the number of carbon atoms increased by two, using a D-2-deoxyribose-5-phosphate aldolase having a property of retaining 50% or greater of activity after treating at 25° C. for 30 minutes in an aqueous medium containing 100 mM of chloroacetaldehyde, wherein the D-2-deoxvribose-5-phosphate aldolase comprises SEQ ID NO: 2 or SEQ ID NO: 4.

2. The process according to claim 1, wherein the substituted or unsubstituted aliphatic aldehyde compound having 2 to 6 carbon atoms is a compound represented by General Formula (1), General Formula (2) or General Formula (3), and the corresponding aldehyde compound having the number of carbon atoms increased by two, which is obtained by aldol condensation, is an aldehyde compound represented by General Formula (4), General Formula (5) or General Formula (6), respectively:

wherein in General Formula (1) to General Formula (6), $R_1$ is a hydrogen atom, a hydroxyl group, a halogen atom, an azido group, a carboxyl group, or an alkyl group, an alkoxy group or an alkanoic acid group respectively having 1 to 4 carbon atoms; $R_2$ is a hydrogen atom, a hydroxyl group or a methyl group; and $R_3$ is a hydrogen atom or a hydroxyl group.

3. The process according to claim 2, wherein acetaldehyde is used in an amount ranging from 0.5 molar equivalents to 3.0 molar equivalents based on an amount of the compound represented by General Formula (1), General Formula (2) or General Formula (3).

4. The process according to claim 3, wherein D-2-deoxyribose-5-phosphate aldolase is used at a ratio of 0.1 U/mmol to 80 U/mmol (1 U represents the amount of enzyme which decomposes 1 μmol of D-2-deoxyribose-5-phosphate into D-glyceraldehyde-3-phosphate and acetaldehyde at 25° C. in 1 minute), relative to the total number of moles of the aldehyde compound represented by General Formula (1), General Formula (2) or General Formula (3), and acetaldehyde.

5. The process according to claim 4, wherein the aldehyde compound represented by General Formula (1), General Formula (2) or General Formula (3) is an aldehyde selected from acetaldehyde, chloroacetaldehyde, glycolaldehyde, propionaldehyde, butylaldehyde, isobutylaldehyde, 3,4-dihydroxybutylaldehyde, malonate semialdehyde, succinate semialdehyde and adipate semialdehyde.

6. A process for producing a compound represented by General Formula (7), comprising conducting aldol condensation of a compound represented by General Formula (1) with two molecules of acetaldehyde to produce a compound represented by General Formula (7), having the number of carbon atoms increased by four, using D-2-deoxvribose-5-phosphate aldolase having a property of retaining 50% or greater of activity after treating at 25° C. for 30 minutes in an aqueous medium containing 100 mM of chloroacetaldehyde, wherein the D-2-deoxyribose-5-phosphate aldolase comprises SEQ ID NO: 2 or SEQ ID NO: 4 wherein in General Formula (7), General Formulae (1) and (7), $R_1$ is a hydrogen atom, a hydroxyl group, a halogen atom, an azido group, a carboxyl group, or an alkoxy group having 1 to 4 carbon atoms.

7. The process according to claim 6, wherein D-2-deoxyribose-5-aldolase is used for the reaction at a ratio of 0.1 U/mmol to 120 U/mmol (1 U represents the amount of enzyme which decomposes 1 μmol of D-2-deoxyribose-5-phosphate into D-glyceraldehyde-3-phosphate and acetaldehyde at 25° C. in 1 minute), relative to the total number of moles of the compound represented by General Formula (1)

and acetaldehyde (in General Formula (7), $R_1$ is a hydrogen atom, a hydroxyl group, a halogen atom, an azido group, a carboxyl group, or an alkoxy group having 1 to 4 carbon atoms).

8. The process according to claim 7, wherein the compound represented by General Formula (1) is an aldehyde selected from acetaldehyde, chloroacetaldehyde, glycolaldehyde, propionaldehyde, butylaldehyde, 3,4-dihydroxybutylaldehyde, malonate semialdehyde, succinate semialdehyde, and adipate semialdehyde.

* * * * *

SEQUENCE LISTING

```
<160> NUMBER OF SEQ ID NOS: 10

<210> SEQ ID NO 1
<211> LENGTH: 747
<212> TYPE: DNA
<213> ORGANISM: Thermotoga maritima
<220> FEATURE:
<221> NAME/KEY: CDS
<222> LOCATION: (1)..(744)

<400> SEQUENCE: 1
```

```
atg ata gag tac agg att gag gag gca gta gcg aag tac aga gag ttc      48
Met Ile Glu Tyr Arg Ile Glu Glu Ala Val Ala Lys Tyr Arg Glu Phe
 1               5                  10                  15 tac gaa ttc aag ccc gtc aga gaa agc gca ggt att gaa gat gtg aaa      96
Tyr Glu Phe Lys Pro Val Arg Glu Ser Ala Gly Ile Glu Asp Val Lys
             20                  25                  30 agt gct ata gag cac acg aat ctg aaa ccg ttt gcc aca cca gac gat     144
Ser Ala Ile Glu His Thr Asn Leu Lys Pro Phe Ala Thr Pro Asp Asp
         35                  40                  45 ata aaa aaa ctc tgt ctt gaa gca agg gaa aat cgt ttc cat gga gtc     192
Ile Lys Lys Leu Cys Leu Glu Ala Arg Glu Asn Arg Phe His Gly Val
     50                  55                  60 tgt gtg aat ccg tgt tat gtg aaa ctg gct cgt gaa gaa ctc gaa gga     240
Cys Val Asn Pro Cys Tyr Val Lys Leu Ala Arg Glu Glu Leu Glu Gly
 65                  70                  75                  80 acc gat gtg aaa gtc gtc acc gtt gtt ggt ttt cca ctg gga gcg aac     288
Thr Asp Val Lys Val Val Thr Val Val Gly Phe Pro Leu Gly Ala Asn
                 85                  90                  95 gaa act cgg acg aaa gcc cat gag gcg att ttc gct gtt gag agt gga     336
Glu Thr Arg Thr Lys Ala His Glu Ala Ile Phe Ala Val Glu Ser Gly
            100                 105                 110 gcc gat gag atc gat atg gtc atc aac gtt ggc atg ctc aag gca aag     384
Ala Asp Glu Ile Asp Met Val Ile Asn Val Gly Met Leu Lys Ala Lys
        115                 120                 125 gag tgg gag tac gtt tac gag gat ata aga agt gtt gtc gaa tcg gtg     432
Glu Trp Glu Tyr Val Tyr Glu Asp Ile Arg Ser Val Val Glu Ser Val
    130                 135                 140 aaa gga aaa gtt gtg aag gtg atc atc gaa acg tgc tat ctg gat acg     480
Lys Gly Lys Val Val Lys Val Ile Ile Glu Thr Cys Tyr Leu Asp Thr
145                 150                 155                 160 gaa gag aag ata gcg gcg tgt gtc att tcc aaa ctt gct gga gct cat     528
Glu Glu Lys Ile Ala Ala Cys Val Ile Ser Lys Leu Ala Gly Ala His
                165                 170                 175 ttc gtg aag act tcc acg gga ttt gga aca gga ggg gcg acc gca gaa     576
Phe Val Lys Thr Ser Thr Gly Phe Gly Thr Gly Gly Ala Thr Ala Glu
            180                 185                 190 gac gtt cat ctc atg aaa tgg atc gtg gga gat gag atg ggt gta aaa     624
Asp Val His Leu Met Lys Trp Ile Val Gly Asp Glu Met Gly Val Lys
        195                 200                 205 gct tcc gga ggg atc aga acc ttc gag gac gct gtt aaa atg atc atg     672
Ala Ser Gly Gly Ile Arg Thr Phe Glu Asp Ala Val Lys Met Ile Met
    210                 215                 220 tac ggt gct gat aga ata gga acg agt tcg gga gtt aag atc gtt cag     720
Tyr Gly Ala Asp Arg Ile Gly Thr Ser Ser Gly Val Lys Ile Val Gln
225                 230                 235                 240 ggg gga gaa gag aga tat gga ggt tga                                 747
Gly Gly Glu Glu Arg Tyr Gly Gly
                245
```

<210> SEQ ID NO 2
<211> LENGTH: 248
<212> TYPE: PRT
<213> ORGANISM: Thermotoga maritima

<400> SEQUENCE: 2

```
Met Ile Glu Tyr Arg Ile Glu Glu Ala Val Ala Lys Tyr Arg Glu Phe
 1               5                  10                  15

Tyr Glu Phe Lys Pro Val Arg Glu Ser Ala Gly Ile Glu Asp Val Lys
             20                  25                  30
```

```
Ser Ala Ile Glu His Thr Asn Leu Lys Pro Phe Ala Thr Pro Asp Asp
         35                  40                  45

Ile Lys Lys Leu Cys Leu Glu Ala Arg Glu Asn Arg Phe His Gly Val
 50                  55                  60

Cys Val Asn Pro Cys Tyr Val Lys Leu Ala Arg Glu Glu Leu Glu Gly
 65                  70                  75                  80

Thr Asp Val Lys Val Thr Val Val Gly Phe Pro Leu Gly Ala Asn
                 85                  90                  95

Glu Thr Arg Thr Lys Ala His Glu Ala Ile Phe Ala Val Glu Ser Gly
            100                 105                 110

Ala Asp Glu Ile Asp Met Val Ile Asn Val Gly Met Leu Lys Ala Lys
        115                 120                 125

Glu Trp Glu Tyr Val Tyr Glu Asp Ile Arg Ser Val Val Glu Ser Val
    130                 135                 140

Lys Gly Lys Val Val Lys Val Ile Glu Thr Cys Tyr Leu Asp Thr
145                 150                 155                 160

Glu Glu Lys Ile Ala Ala Cys Val Ile Ser Lys Leu Ala Gly Ala His
                165                 170                 175

Phe Val Lys Thr Ser Thr Gly Phe Gly Thr Gly Gly Ala Thr Ala Glu
            180                 185                 190

Asp Val His Leu Met Lys Trp Ile Val Gly Asp Glu Met Gly Val Lys
        195                 200                 205

Ala Ser Gly Gly Ile Arg Thr Phe Glu Asp Ala Val Lys Met Ile Met
    210                 215                 220

Tyr Gly Ala Asp Arg Ile Gly Thr Ser Ser Gly Val Lys Ile Val Gln
225                 230                 235                 240

Gly Gly Glu Glu Arg Tyr Gly Gly
                245

<210> SEQ ID NO 3
<211> LENGTH: 681
<212> TYPE: DNA
<213> ORGANISM: Pyrobaculum aerophilum
<220> FEATURE:
<221> NAME/KEY: CDS
<222> LOCATION: (1)..(678)

<400> SEQUENCE: 3 atg ata cat tta gta gac tac gcg ctt ctc aag ccg tat ctc aca gta      48
Met Ile His Leu Val Asp Tyr Ala Leu Leu Lys Pro Tyr Leu Thr Val
  1               5                  10                  15 gat gaa gca gtc gcc ggg gct cgc aag gcg gag gag ctg ggc gtc gcg      96
Asp Glu Ala Val Ala Gly Ala Arg Lys Ala Glu Glu Leu Gly Val Ala
                 20                  25                  30 gcg tat tgc gta aat ccc ata tac gcc cct gtt gtt cgg cct ttg ttg     144
Ala Tyr Cys Val Asn Pro Ile Tyr Ala Pro Val Val Arg Pro Leu Leu
             35                  40                  45 cgg aaa gta aag ctc tgc gta gtg gcg gac ttc ccc ttt ggg gcc ttg     192
Arg Lys Val Lys Leu Cys Val Val Ala Asp Phe Pro Phe Gly Ala Leu
         50                  55                  60 cca acg gcc agc aga att gcc ttg gtt tct agg ctt gct gaa gtg gca     240
Pro Thr Ala Ser Arg Ile Ala Leu Val Ser Arg Leu Ala Glu Val Ala
 65                  70                  75                  80 gat gag ata gac gtg gtg gcg cct ata ggc ctc gtg aaa tcg cgg agg     288
Asp Glu Ile Asp Val Val Ala Pro Ile Gly Leu Val Lys Ser Arg Arg
                 85                  90                  95 tgg gcc gag gtg aga agg gac tta ata agc gtt gtg ggt gcc gca ggc     336
Trp Ala Glu Val Arg Arg Asp Leu Ile Ser Val Val Gly Ala Ala Gly
```

-continued

```
                100                 105                 110
ggg aga gtg gta aag gta atc aca gag gag cct tat cta agg gat gag    384
Gly Arg Val Val Lys Val Ile Thr Glu Glu Pro Tyr Leu Arg Asp Glu
        115                 120                 125 gag agg tat acg ctt tac gac att att gca gag gct ggg gcc cac ttt    432
Glu Arg Tyr Thr Leu Tyr Asp Ile Ile Ala Glu Ala Gly Ala His Phe
    130                 135                 140 ata aaa agc tcc act gga ttc gcc gaa gag gcc tac gcc gcc aga cag    480
Ile Lys Ser Ser Thr Gly Phe Ala Glu Glu Ala Tyr Ala Ala Arg Gln
145                 150                 155                 160 gga aat cct gta cac tca acg ccg gag agg gcg gcg gca att gcc cgc    528
Gly Asn Pro Val His Ser Thr Pro Glu Arg Ala Ala Ala Ile Ala Arg
                165                 170                 175 tac ata aaa gag aag ggg tat aga ctg ggg gtg aaa atg gcg ggg ggg    576
Tyr Ile Lys Glu Lys Gly Tyr Arg Leu Gly Val Lys Met Ala Gly Gly
            180                 185                 190 att agg aca agg gag cag gca aag gcc att gtt gac gcc att gga tgg    624
Ile Arg Thr Arg Glu Gln Ala Lys Ala Ile Val Asp Ala Ile Gly Trp
        195                 200                 205 ggc gag gac cca gcc cgc gtc agg ctg ggg acg tcc acc cca gag gct    672
Gly Glu Asp Pro Ala Arg Val Arg Leu Gly Thr Ser Thr Pro Glu Ala
    210                 215                 220 ctt cta tag                                                        681
Leu Leu
225

<210> SEQ ID NO 4
<211> LENGTH: 226
<212> TYPE: PRT
<213> ORGANISM: Pyrobaculum aerophilum

<400> SEQUENCE: 4

Met Ile His Leu Val Asp Tyr Ala Leu Leu Lys Pro Tyr Leu Thr Val
  1               5                  10                  15

Asp Glu Ala Val Ala Gly Ala Arg Lys Ala Glu Glu Leu Gly Val Ala
                 20                  25                  30

Ala Tyr Cys Val Asn Pro Ile Tyr Ala Pro Val Arg Pro Leu Leu
             35                  40                  45

Arg Lys Val Lys Leu Cys Val Val Ala Asp Phe Pro Phe Gly Ala Leu
     50                  55                  60

Pro Thr Ala Ser Arg Ile Ala Leu Val Ser Arg Leu Ala Glu Val Ala
 65                  70                  75                  80

Asp Glu Ile Asp Val Val Ala Pro Ile Gly Leu Val Lys Ser Arg Arg
                 85                  90                  95

Trp Ala Glu Val Arg Arg Asp Leu Ile Ser Val Val Gly Ala Ala Gly
             100                 105                 110

Gly Arg Val Val Lys Val Ile Thr Glu Glu Pro Tyr Leu Arg Asp Glu
         115                 120                 125

Glu Arg Tyr Thr Leu Tyr Asp Ile Ile Ala Glu Ala Gly Ala His Phe
     130                 135                 140

Ile Lys Ser Ser Thr Gly Phe Ala Glu Glu Ala Tyr Ala Ala Arg Gln
145                 150                 155                 160

Gly Asn Pro Val His Ser Thr Pro Glu Arg Ala Ala Ala Ile Ala Arg
                 165                 170                 175

Tyr Ile Lys Glu Lys Gly Tyr Arg Leu Gly Val Lys Met Ala Gly Gly
             180                 185                 190

Ile Arg Thr Arg Glu Gln Ala Lys Ala Ile Val Asp Ala Ile Gly Trp
```

```
                195                 200                 205
Gly Glu Asp Pro Ala Arg Val Arg Leu Gly Thr Ser Thr Pro Glu Ala
    210                 215                 220

Leu Leu
225

<210> SEQ ID NO 5
<211> LENGTH: 30
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 5
tatatcatat gatagagtac aggattgagg                                           30

<210> SEQ ID NO 6
<211> LENGTH: 30
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 6
taatggatcc tcaacctcca tatctctctt                                           30

<210> SEQ ID NO 7
<211> LENGTH: 30
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 7
tatatcatat gatacattta gtagactacg                                           30

<210> SEQ ID NO 8
<211> LENGTH: 30
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 8
taatggatcc ctatagaaga gcctctgggg                                           30

<210> SEQ ID NO 9
<211> LENGTH: 30
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 9
tatactatat gactgatctg aaagcaagca                                           30

<210> SEQ ID NO 10
<211> LENGTH: 30
<212> TYPE: DNA
<213> ORGANISM: Artificial Sequence
<220> FEATURE:
```

```
<223> OTHER INFORMATION: Description of Artificial Sequence: Synthetic
      Primer

<400> SEQUENCE: 10
taatggatcc ttagtagctg ctggcgctct                                              30
```